US006951573B1

(12) United States Patent
Dilling

(10) Patent No.: US 6,951,573 B1
(45) Date of Patent: Oct. 4, 2005

(54) PROSTHETIC AORTIC VALVE

(76) Inventor: Emery W. Dilling, 6800 Austin Center Blvd., Number 761, Austin, TX (US) 78731

( * ) Notice: Subject to any disclaimer, the term of this patent is extended or adjusted under 35 U.S.C. 154(b) by 114 days.

(21) Appl. No.: 10/028,336

(22) Filed: Dec. 22, 2001

(51) Int. Cl.⁷ .............................................. A61F 2/06
(52) U.S. Cl. ...................................... 623/2.2; 623/2.1
(58) Field of Search .................... 623/2.1, 2.12–2.42

(56) References Cited

U.S. PATENT DOCUMENTS

| | | | |
|---|---|---|---|
| 3,143,742 A | 8/1964 | Cromie | |
| 3,371,352 A | 3/1968 | Siposs et al. | |
| 3,464,065 A | 9/1969 | Cromie | |
| 4,276,658 A | 7/1981 | Hanson et al. | |
| 4,851,001 A | 7/1989 | Taheri | |
| 5,037,434 A * | 8/1991 | Lane | 623/2.18 |
| 5,385,606 A | 1/1995 | Kowanko | |
| 5,476,510 A * | 12/1995 | Eberhardt et al. | 623/2.11 |
| 5,514,410 A | 5/1996 | Ely et al. | |
| 5,772,694 A | 6/1998 | Bokros et al. | |
| 5,908,451 A * | 6/1999 | Yeo | 623/2.22 |
| 6,059,826 A | 5/2000 | Bokros et al. | |
| 6,106,550 A | 8/2000 | Magovern et al. | |
| 6,245,083 B1 | 6/2001 | Black et al. | |

* cited by examiner

*Primary Examiner*—Thomas Barrett
(74) *Attorney, Agent, or Firm*—Fitch, Even, Tabin & Flannery

(57) ABSTRACT

A prosthetic aortic valve is designed to be implanted in the natural aortic annulus and to extend into the ascending aorta to a point short of the right and left coronary arteries. Blood leakage around the valve is prevented by tension in one or more circumferential cords drawing annular tissue into sealing contact with an external sealing ring on the valve body. The security of the valve's attachment to a patient is assured with a plurality of interrupted sutures between a semirigid flange on the valve outer surface and the patient's aortic commissures and/or the patient's ascending aortic wall. The sutures are preferably attached to posts or cleats on the semirigid sewing flange, the flange being spaced apart from the valve inlet by the sealing ring.

31 Claims, 9 Drawing Sheets

PROSTHETIC AORTIC VALVE

BACKGROUND

The present invention relates to surgically implantable mechanical valves that can replace cardiac valves damaged by disease or injury. In particular, the invention comprises methods and apparatus for total replacement of aortic valves.

Mechanical prosthetic aortic valves are typically attached to the tissue of the natural valve annulus and simulate the function of aortic valve semilunar leaflets, ensuring one-way arterial blood flow out of the left ventricle of the heart. They have been in clinical use for about 50 years, and during that time prosthetic valves' durability and hemodynamic characteristics have been improved significantly. Still, a continued high risk of thromboembolism from the mechanical valves mandates lifelong anticoagulant therapy for patients receiving them. This therapy is costly and inconvenient, and it predisposes patients to a variety of complications that can impair health and shorten life (e.g., stroke arising from either excessive or insufficient anticoagulation).

Over the years, significant reductions in prosthetic valve thrombogenicity have been achieved by, for example, removing fabric that originally covered certain valve structural members (e.g., the cages of cage-ball valves). Further improvements have been made through replacement of valve components formerly comprising plastics and/or certain metals with analogous structural elements made of pyrolytic carbon. With these and other refinements, the service life of prosthetic cardiac valves has been extended to more than 20 years. But one major structural feature found on almost all modern prosthetic mechanical valves continues to cause significant morbidity and mortality. That feature is a fibrous sewing cuff, typically comprising woven and/or felted fibrous material such as Dacron, through which sutures can be placed to retain the valve in place and to prevent leakage of blood around the valve body.

Fibrous sewing cuffs have been recognized for decades as potential sources of infection and strong contributors to thrombogenesis, but they are still commonly used for implanting cardiac valves. One reason for their continued acceptance is the flexibility such sewing cuffs give surgeons to place interrupted valve-retention sutures in the most suitable tissue sites on the annulus, thereby avoiding calcified and otherwise damaged or weakened areas. The resulting sutures, while tedious and time-consuming to place in large numbers, provide needed strength to retain the implanted valve in place and to avoid blood leakage by ensuring a good cuff-to-annulus seal.

Notwithstanding the above-noted advantages of sewing cuffs, cuffless valve designs have been proposed to eliminate fibrous material (thus reducing the risk of infection) and also to shorten the time required to implant a prosthetic valve by eliminating the need for sutures. Examples of such designs are disclosed in U.S. Pat. Nos. 3,143,742 (Cromie) and 6,106,550 (Magovern), both patents incorporated herein by reference. The cuffless valves of the '742 and '550 patents replace sutures with a fixed series of closely spaced peripheral pins for attaching the valve to the annular opening.

While they were initially described as improvements, the valves of the '742 and '550 patents have achieved only limited acceptance. In part, this is because pre-existing disease states (e.g., calcification of the annulus) and a limited range of valve sizes make it difficult in practice to achieve a close and mechanically strong implant attachment to an annulus that has a non-uniform sealing surface (e.g., a sealing surface distorted and/or weakened by calcification). Initial mechanical weakness in such a valve attachment tends to persist, while gaps that result from mismatching the implant and annular diameters allow blood leaks around the valve. The latter leaks may eventually be plugged by an overgrowth of pannus from the annulus, but such pannus overgrowth can also become a source of emboli that pose a threat to the patient.

Troublesome pannus overgrowth on metallic structures of pin-secured valves may be controlled to some extent by adding a preferred growth substrate in the form of a fibrous sewing cuff. The added cuff also provides a way to supplement the strength of the valve's pin attachment with one or more sutures securing the cuff to the annular tissue. See, for example, U.S. Pat. Nos. 3,371,352 (Siposs et al.), and 3,464,065 (Cromie), both patents incorporated herein by reference. Unfortunately, pannus overgrowth cannot be reliably limited exclusively to the sewing cuff, which can lead to the familiar problem of thromboembolus formation. Further, as noted above, the presence of fibrous cuff material provides a nidus for opportunistic infections.

An alternative cuffless valve design that purports to avoid problems related to blood leakage around the implant is described in U.S. Pat. No. 4,851,001 (Taheri), incorporated herein by reference. A valve according to the '001 patent overcomes the blood leakage problems described above because it is secured in a vein with a circumferential cord that compresses the vein wall into close (i.e., sealing) contact with a circumferential groove on the valve body. By drawing the cord sufficiently (but not overly) tight, blood leaks between the valve and vein wall can be eliminated without damaging the vein.

But the Taheri valve is only held in position within a vein by the relatively low frictional forces between the outwardly-directed groove and the vein. This means that while the Taheri valve design may be suitable for relatively low pressures like those commonly encountered in the venous system, it is contraindicated for use with (significantly higher) aortic pressures. In typical patients, venous pressures across a cardiac valve are generally less than about 20 torr, but an aortic valve may experience analogous pressures of more than 250 torr in the forward flow direction, and nearly 100 torr in the reverse flow direction. These higher pressures would tend to catastrophically dislodge the entire Taheri valve if it were placed in the aorta because the valve is not secured by either sutures or pins. In apparent recognition of this design limitation, in vivo tests described in the '001 patent refer only to prosthetic valve implantations in jugular veins of dogs.

A further indication of the low-pressure applications for which the Taheri valve was designed is found in the detailed description of the '001 patent's FIG. 8. The differential pressure across the valve between heartbeats is described as being small enough to permit gravity to return plate 96 from the open to the closed position. While such small pressure differentials may be found in portions of the venous system, they are totally inconsistent with normal (i.e., substantially higher) pressures across aortic valves.

The preceding discussion suggests that, notwithstanding the many alternative designs proposed to date, an ideal prosthetic cardiac valve is not yet available. In particular, a new aortic valve is needed that avoids the well-known disadvantages of a fibrous cuff. Further, the new valve should be securely implantable using the strength and flexibility of sutures, and a patient should experience no significant blood leakage around the valve after implantation.

SUMMARY OF INVENTION

Prosthetic valves of the present invention comprise a substantially round tubular valve body containing internal flow control means and having a generally circular cross section. The valve body has a longitudinal axis, an outlet end, an inlet end, an inner surface, and an outer surface. On the valve body's outer surface, a semirigid flange is spaced apart from the inlet end by a circumferential sealing ring. In preferred embodiments having a flared inlet end, the sealing ring has the shape of a groove that is sized (including a width and minimum diameter) to closely fit the shape of a patient's natural aortic valve annulus.

The inlet end of the tubular valve body is preferably flared out to a diameter larger than that of the natural annular opening or, alternatively, is substantially cylindrical (i.e., not flared out). When a flared inlet end is inserted through the annulus (by slightly and reversibly distending the annulus), the outer surface of the flared inlet end can then be closely approximated to the intra-cardiac portion of the annulus. The flared inlet end, when present, is structurally similar to (but not necessarily dimensionally identical to) the flared entrance section 19 shown and described in U.S. Pat. No. 5,772,694 (Bokros et al.), incorporated herein by reference.

Valves of the present invention reduce or eliminate the problems of thrombogenesis and infection described in the background because they have no circumferential fibrous sewing cuffs. Thus, the troublesome contact between fibrous cuff material and the patient's blood stream that is common with earlier valves is eliminated in valves of the present invention. Instead of a fibrous sewing cuff, separate structures are used for the essential functions of securing an implanted valve in a patient and sealing it against blood leakage around the valve body. These separate structures comprise a semirigid sewing flange for the securing function and an external circumferential sealing ring for the sealing function.

Rather than providing for sutures through a fibrous sewing cuff to attach a prosthetic valve to tissue immediately surrounding a patient's natural annular opening, as in earlier valve designs, the semirigid sewing flange of the present invention facilitates securing a valve to a patient's aortic valve commissures instead. The commissures are located distal to the annular opening, so a semirigid sewing flange is preferably spaced relatively farther apart from the valve inlet than a fibrous cuff would be. The increased spacing is sufficient to accommodate a circumferential sealing ring on the valve body outer surface between the semirigid flange and the valve inlet.

On implantation of a valve of the present invention, a plurality of generally radial interrupted sutures are placed between one or more holes or notches in the sewing flange and adjacent aortic valve commissures. The commissures, usually three in number, are the areas where the natural aortic valve semilunar leaflets meet, and they comprise relatively dense and tough tissue similar to that immediately surrounding the natural aortic annular opening. Thus, securing a valve by interrupted sutures through the commissures prevents clinically significant translation or rotation of the valve with respect to important anatomic structures, such as the annulus and the coronary arteries, after implantation.

In preparing a patient for aortic valve replacement with a valve of the present invention, the natural semilunar leaflets are excised, but the commissures remain undisturbed and are thus generally available for securing the valve. Note that while the commissures have always been available to cardiac surgeons performing aortic valve replacements, they have only been used incidently in the past for securing fibrous-cuffed valves. This is because the commissures alone can not provide for a complete circumferential line of sutures necessary for sealing a fibrous cuff to the annular tissue. Such a complete suture line, of course, was necessary in older valves with fibrous cuffs to accomplish the dual functions of securing the valve and simultaneously blocking blood leakage around the valve. Unfortunately, as described above, use of fibrous sewing cuffs in this manner increases the risk of both infections and thromboembolism.

Since valves of the present invention do not have fibrous sewing cuffs, the function of blocking blood leakage around an implanted valve is facilitated instead by a circumferential sealing ring that lies between the semirigid sewing flange and the valve inlet. After implantation, this sealing ring will lie in close contact with, and preferably adhere to, the tissue of the patient's natural aortic valve annulus. To enhance adherence, and thus sealing, of annular tissue to the sealing ring, preferred embodiments of the sealing ring may comprise a circumferential tissue adherence band. On the outer surface of a valve body that otherwise comprises polished pyrolytic carbon, for example, the circumferential sealing ring may comprise, in turn, a circumferential tissue adherence band of unpolished pyrolytic carbon.

The purpose of the tissue adherence band is to encourage intimate contact of aortic annular tissue with the band, primarily to block blood leakage around the valve body (i.e., leakage between the sealing ring on the valve body outer surface and the annulus). The sealing function of the tissue adherence band is fostered in preferred embodiments by annular tissue growth into surface irregularities of the tissue adherence band. Such tissue ingrowth strengthens adhesion of the natural valve annular tissue to the band and thus to the valve body, thereby tending to prevent blood leakage around the valve.

A circumferential external tissue adherence band (when present) preferably lies within a circumferential groove formed on the valve body outer surface between the inlet end outward flare (when present) and the semirigid flange. This groove is preferably sized to fit the natural annular opening (i.e., having a groove width in the range of about 4 mm to about 12 mm).

The presence or absence of a groove may be preferred by surgeons, depending on the condition of the patient's commissures. As noted above, interrupted sutures connecting the commissures to the semirigid flange are preferred to secure the valve in place. When a surgeon believes that this securing function should be augmented by the additional stabilization offered by placement of the aortic annulus in a groove as described above, then a valve with a flared inlet end and the appropriate groove width may be chosen for the patient.

Preferred materials for a tissue adherence band may also be a matter of the surgeon's choice, depending primarily on the condition of the patient's annular sealing surface (i.e., the surface of the natural annular opening that will be in contact with the tissue adherence band). During implantation of valves of the present invention, annular tissue is drawn into sealing contact with the circumferential sealing ring (and thus into sealing contact with the tissue adherence band, if present) by one or more circumferential tensioning cords. These cords lie within the annular tissue and/or around the portion of the ascending aortic wall just distal to the annular tissue. Normally, the sealing contact achieved through the action of the circumferential tensioning cord(s) on the annular tissue will be sufficient to block blood leakage around the valve (that is, blood leakage between the annular tissue and the sealing ring). When the sealing ring comprises a circumferential tissue adherence band, additional sealing action is achieved through growth of annular tissue into irregular surface features on the tissue adherence band. Such growth of tissue into the tissue adherence band surface enhances the sealing function of the tensioning cord(s).

A preferred form of surface irregularities on a tissue adherence band is provided by, for example, an unpolished circumferential pyrolytic carbon band on the external surface of the valve body. However, a surgeon may conclude after inspecting a patient's annular tissue surface that a different type of tissue adherence band surface irregularity may be needed to encourage annular tissue ingrowth. Such a different type of surface irregularity may be furnished, for example, by a fibrous tissue adherence band of material such as Dacron fiber.

Where non-fibrous material (such as unpolished pyrolytic carbon) or fibrous material (such as Dacron fiber) is used to enhance tissue adherence in prosthetic valves of the present invention, the fibrous or non-fibrous material is preferably located where, after valve implantation, it will be blocked from contact with the bloodstream by valve structures and/or by the patient's tissues. Thus, a circumferential fibrous or non-fibrous tissue adherence band on the outer surface of the valve body will preferably be sufficiently narrow so that after implantation a patient's annular tissue will overlap the band on both sides, thus blocking contact of the fibrous material of the band with the bloodstream.

Where desirable, additional or alternative means of blocking bloodstream contact with a tissue adherence area on valves of the present invention may be used. An example of such alternative means is a tissue adherence area partially bordered by or completely circumscribed by a shield margin. The shield margin in this example comprises a relatively non-thrombogenic sealing surface, i.e., a sealing surface that is less thrombogenic than the tissue adherence area itself. Such shield margins may be employed, for example, on cleats or posts of a semirigid flange.

Because sutures connecting cleats and posts to a patient's commissures function to secure preferred embodiments of an implanted valve, strong adherence between the patient's tissue and the tissue contact surfaces of cleats and posts may be deemed desirable by the surgeon implanting the valve. And whereas materials with tissue adherence properties similar to those of unpolished pyrolytic carbon may be adequate, stronger tissue adherence may be beneficial for some patients. In such patients, fibrous material may be employed in areas circumscribed or partially bordered by shield margins. The combination of a tissue adherence area and its shield margin is called a shielded fibrous insert.

Normally, shielded fibrous inserts would be used, if needed, on tissue-contact surfaces of semirigid flanges because of the added mechanical strength they can confer on the sutured connection between a flange and a patient's tissue. Regardless of how (or whether) shielded fibrous inserts are used on valves of the present invention, careful attention is given to blocking contact between a patient's bloodstream and any fibrous material on implanted valves. By blocking such contact, the benefits of selective use of fibrous materials can be obtained while additional risks of infection and/or thromboembolism are minimized or eliminated.

DETAILED DESCRIPTION

Figure 1:
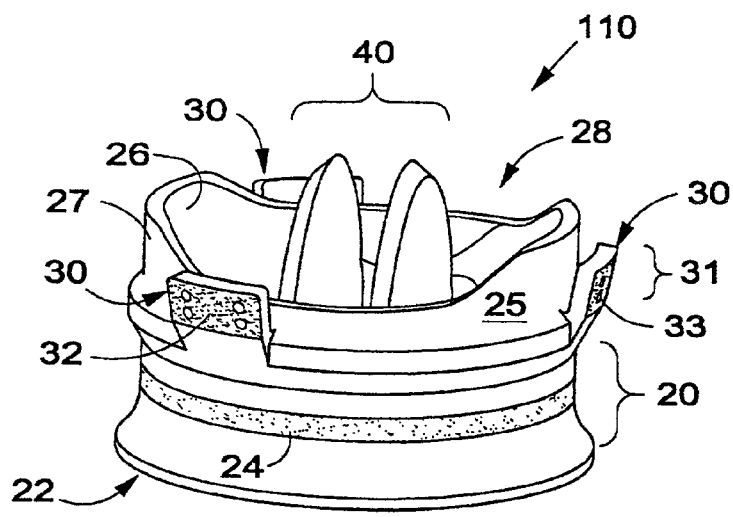
FIG. 1 schematically illustrates a valve of the present invention comprising a flared inlet end, a non-fibrous tissue adherence band on the external circumferential valve body groove, and non-fibrous tissue adherence areas on tissue contact surfaces of the semirigid flange posts.

A semirigid sewing flange of the present invention allows placement of a plurality of interrupted sutures for securing a prosthetic valve to the aortic valve commissures and/or to the ascending aortic wall between the commissures. Since the commissures themselves are generally not evenly spaced around the annulus, the interrupted sutures are generally not evenly spaced either. Thus, while suitable for the valve securing function, these interrupted sutures are not preferred for the function of sealing to prevent blood leakage around an implanted prosthetic valve.

The function of sealing to prevent blood leakage around implanted valves of the present invention is provided by tension in one or more circumferential tensioning cords. Each such tensioning cord is placed within the tissue surrounding a patient's aortic annular opening (as, for example, by one or more purse-string sutures placed within the tissue) and/or around the ascending aortic wall distal to the aortic annulus. Tension in the cord(s) draws the annular tissue into sealing contact with a sealing ring (that may comprise a tissue adherence band) on the valve's outer surface. This sealing function is substantially separate in valves of the present invention from the securing function.

The securing function, as noted above, relates to the strength of the valve's attachment to anatomic structures such as the commissures, as well as the stability of the valve's position with respect to anatomic structures such as the annulus and the coronary arteries. Secure attachment of implanted valves of the present invention is primarily assured by the plurality of interrupted sutures connecting the semirigid sewing flange(s) to the commissures and/or to the ascending aortic wall between the commissures.

Semirigid flange embodiments of the present invention preferably comprise a solid material that is tough and flexible in thin sections and relatively non-thrombogenic compared to fibrous materials such as Dacron fiber. Since, after implantation, the arcuate (i.e., curved) portions of the semirigid flange(s) lie between the similarly curved tubular valve body and the generally tubular ascending aortic wall and commissure tissues, the latter structures naturally conform closely to each arcuate flange portion with relatively little tissue distortion. Further, since the valve body preferably has the largest cross-sectional area practically achievable within a patient's aortic annulus (to minimize resistance to blood flow through the valve), arcuate portions of semirigid flange are preferably relatively thin but still strong enough to ensure secure attachment of the valve to the patient. A preferred material for such a semirigid flange and for the underlying valve body is pyrolytic carbon. Pyrolytic carbon (Pyrocarbon) is described in U.S. Pat. No. 5,514,410 (Ely et al.), incorporated herein by reference.

Semirigid flanges may be discontinuous, continuous, and/or contiguous in various preferred embodiments. When they are contiguous or discontinuous, semirigid flanges preferably comprise the same solid material (e.g., pyrolytic carbon) as that of the tubular valve body. In such embodiments, the flange preferably arises directly from, and comprises the same material as, the valve body. This obviates any requirement for additional means (comprising, for example, adhesives, rivets or other mechanical means) for connecting a flange to the valve body. However, when a semirigid flange is continuous it may alternatively comprise the same solid material as that of the tubular valve body or a different material. For example, a continuous stainless steel circumferential semirigid flange ring may be tightly secured in place on a valve body, as by use of adhesives or by shrink fitting of the stainless steel ring to a valve body.

When a semirigid flange has the form of a contiguous coplanar or non-coplanar ring around a pyrolytic carbon valve body, the contiguous areas (i.e., areas where the flange ring is thinned for added flexibility) allow the tubular valve body to be temporarily and reversibly flexed (i.e., slightly deformed). Such deformation is often useful with pyrolytic carbon valve bodies to allow placement of internal valve flow control means structures, such as leaflets (which may also comprise pyrolytic carbon) within the tubular valve body.

Depending on a patient's individual anatomy, a discontinuous or non-coplanar contiguous semirigid sewing flange may preferably be used in the region of the right and left coronary artery ostia, which lie in the ascending aortic wall a short distance downstream of (i.e., distal to) the outlet end of the tubular valve body. In such embodiments, flange spacing from the ostia is preferably increased to minimize the likelihood of the flange impinging on the right and/or left coronary arteries, which could thereby compromise blood flow to the heart muscle itself.

To reduce any potential for interference with blood flow in the right and left coronary arteries, discontinuous embodiments of a semirigid sewing flange comprise at least first and second arcuate flange portions that may, in alternative preferred embodiments, be substantially coplanar or substantially non-coplanar. The flange portions are arcuate in that they closely follow the rounded contour of the tubular valve body to minimize space between the valve body outer wall and adjacent tissues after implantation. To reduce the likelihood of coronary blood flow compromise, discontinuous arcuate flange portions are preferably spaced apart from each other in the regions of a valve body outer surface near where the right and left coronary ostia will lie after implantation of the valve.

In preferred embodiments of valves of the present invention, a plurality of arcuate flange portions comprise at least one cleat and/or at least one post to secure suture material for connecting the post or cleat to the patient's commissures and/or ascending aortic wall. A post or cleat arises from, and thus is integrally connected to, the portion of an arcuate flange portion that itself is integral with or otherwise securely connected to a valve body. But posts and cleats are spaced apart from the valve body sufficiently to allow securing of sutures through one or more holes (in the case of a post) or around at least one notch (in the case of a cleat). Preferred embodiments of cleats comprise two notches for securing suture material that may then be alternately passed through the two notches in succession. Posts and cleats may be located individually on a flange or may be grouped to provide flexibility in placement of sutures in a variety of patients having slightly different spacing between their commissures.

A semirigid flange of the present invention is located relatively closer to the outlet end of a tubular valve body than to the inlet end. This position is important so that at least one of the associated cleat(s) and/or post(s) (in embodiments having cleats or posts) will be adjacent to each of a patient's commissures when the prosthetic valve sealing ring is properly positioned in the patient's aortic valve annulus. This means that at least one post or cleat will preferably be located on or about a radial line extending from the valve body longitudinal axis and passing through each commissure. Generally radial sutures can then firmly attach the post(s) and/or cleat(s) to the respective commissures and/or to the ascending aortic wall that lies between the commissures. Sutures to the ascending aortic wall are intended to supplement the strength of sutures to the commissures where the surgeon deems they are needed due, for example, to disease and/or anatomic anomalies in the patient's commissures.

These substantially radial suture attachments secure a semirigid flange, and thus the tubular valve body itself, in the desired position for a valve implant. The sutures collectively function to prevent the valve body from moving clinically significant distances upstream (i.e., toward the heart) or clinically significant distances downstream (i.e., toward the coronary arteries). In the latter function, the flared inlet end of the valve tubular body, when present and resting closely against the intra-cardiac surface of the natural aortic annulus, aids in preventing the valve body from moving downstream.

Regardless of the form a semirigid flange of the present invention may take, fibrous materials may preferably be used to enhance the valve-securing function of the flanges. When so used, the fibrous materials are preferably adhered (i.e., bonded, as with biocompatible adhesives) to limited areas of the flanges such as the tissue contact surfaces of suturing posts or cleats. When so used, fibrous materials function to increase the strength of valve attachment to a patient through tissue ingrowth among the fibers.

In such applications, fibrous materials may be effectively shielded from contact with the blood stream by, for example, a patient's tissue that overlaps a tissue contact surface on a cleat or post after valve implantation. Alternatively or supplementally, a shield margin may be employed comprising fused fibers (e.g., fused Dacron). Another preferred form of a shield margin comprises the material of the post or cleat itself (e.g., pyrolytic carbon or stainless steel). Shielded fibrous inserts can thus be used increase the stability of valve attachment by encouraging vigorous tissue ingrowth, while minimizing or eliminating any additional risk of infection and/or thromboembolism due to the presence of fibrous materials in contact with the blood stream. In this respect, shielded fibrous inserts differ significantly from earlier fibrous sewing cuffs. The inserts are so constructed as not to expose clinically significant amounts of fibrous materials such as felted or woven fabric to the blood stream, whereas older fibrous sewing cuffs necessarily expose relatively large fibrous areas to blood flow because the cuffs serve the dual functions of securing a valve and sealing against blood leakage around the valve.

In the present invention, structures supporting the function of sealing against blood leakage, e.g., a circumferential sealing ring (that may comprise a circumferential tissue adherence band) on the external surface of a valve body, are spatially separated from structures for securing the valve, e.g., posts on a plurality of arcuate portions of a discontinuous semirigid flange. Materials such as unpolished pyrolytic carbon have tissue adhesion properties to support their use for a tissue adherence band on a prosthetic valve for an otherwise healthy patient. But where tissue adhesion may be impaired, as by disease or anatomic anomaly, biocompatible fibrous materials such as Dacron, for example, may be used to improve tissue adhesion, and thus sealing, to a circumferential tissue adherence band.

Conversely, where tissue adhesion to a tissue contact surface (such as that on a post or cleat or circumferential sealing ring) does not require enhanced strength, tissue adherence areas (comprising, e.g., unpolished pyrolytic carbon or Dacron fiber) need not be used on such a surface. The requirement, if any, for enhanced tissue adhesion strength at such tissue contact surfaces is determined by the surgeon who implants the valve.

Thus, when valves of the present invention are implanted in a patient, the patient's aortic annulus seals against a circumferential sealing ring on the external surface of the tubular valve body. This sealing ring, as noted above, preferably takes the form of a circumferential groove that lies between a flared inlet end and a semirigid flange. One or more circumferential tensioning cords located as described herein ensure that the annulus is sufficiently sealed against the sealing ring so as to prevent aortic blood leakage around the tubular valve body in the immediate postoperative period as well as during the lifetime of the valve.

To ensure adequate sealing in both the short and longer term without excessive cord tension that could lead to tissue necrosis, a tissue adhesive may preferably be employed between a patient's annular tissue and the sealing ring on the tubular valve body. Similarly, a tissue adhesive may preferably be employed between posts and/or cleats and the tissues they contact for added strength. An example of a suitable tissue adhesive is disclosed in U.S. Pat. No. 5,385,606 (Kowanko), and typical applications of the adhesive are disclosed in U.S. Pat. No. 6,245,083 (Black et al.), both patents incorporated herein by reference.

In addition to the securing and sealing functions discussed above, valves of the present invention must of course control one-way (forward) blood flow through the valves from inlet to outlet. This blood flow control is preferably achieved through use of any of a variety of flow control means well known to those skilled in the art. Such flow control means are retained within the tubular valve body of the present invention and provide intermittent reversible sealing across the valve body inner surface against backflow of blood, alternating with opening of the flow control means to allow forward blood flow.

Examples of the types of flow control means preferred for use in valves of the present invention include, but are not limited to, the three leaflets 13 or the three leaflets 83 together with corresponding structures (i.e., those structures related to their respective retention, support, movement and intermittent sealing function) as illustrated and described in U.S. Pat. No. 6,059,826 (Bokros et al.), incorporated herein by reference. Another example of flow control means preferred for valves of the present invention includes the two leaflets 11 and 12 and their corresponding structures as illustrated and described in U.S. Pat. No. 4,276,658 (Hanson et al.), incorporated herein by reference. Still another example of preferred flow control means includes the ball 8 and seat 7 and their corresponding structures as illustrated and described in U.S. Pat. No. 3,143,742 (Cromie), already incorporated herein by reference. And yet another example of preferred flow control means includes the plate 96 and lip 98 and their respective corresponding structures as illustrated and described in U.S. Pat. No. 4,851,001 (Taheri), already incorporated herein by reference.

Representative flow control means comprising the leaflets 40, 40' and 40", together with corresponding structures related to their retention, support, movement and intermittent sealing function, are schematically illustrated in various Figures herein. Other flow control means, including those cited as examples above and other analogous means well known in the art may be used in valves of the present invention.

FIG. 1 schematically illustrates valve 110, including the leaflets 40 and a substantially round tubular valve body 25. Also illustrated are an outlet end 28, a flared inlet end 22, an inner surface 26, an outer surface 27, and a discontinuous semirigid sewing flange comprising the three arcuate portions 30. Each of the arcuate portions 30, in turn, comprises a post 31 having four holes 33 and a non-fibrous tissue adherence area 32. Each tissue adherence area 32 is generally coextensive with the tissue contact surface of the corresponding post 31. Each post 31 is spaced apart from valve body 25 sufficiently to allow suture material to be secured to the post as schematically illustrated, for example, in FIG. 2.

Figure 2:
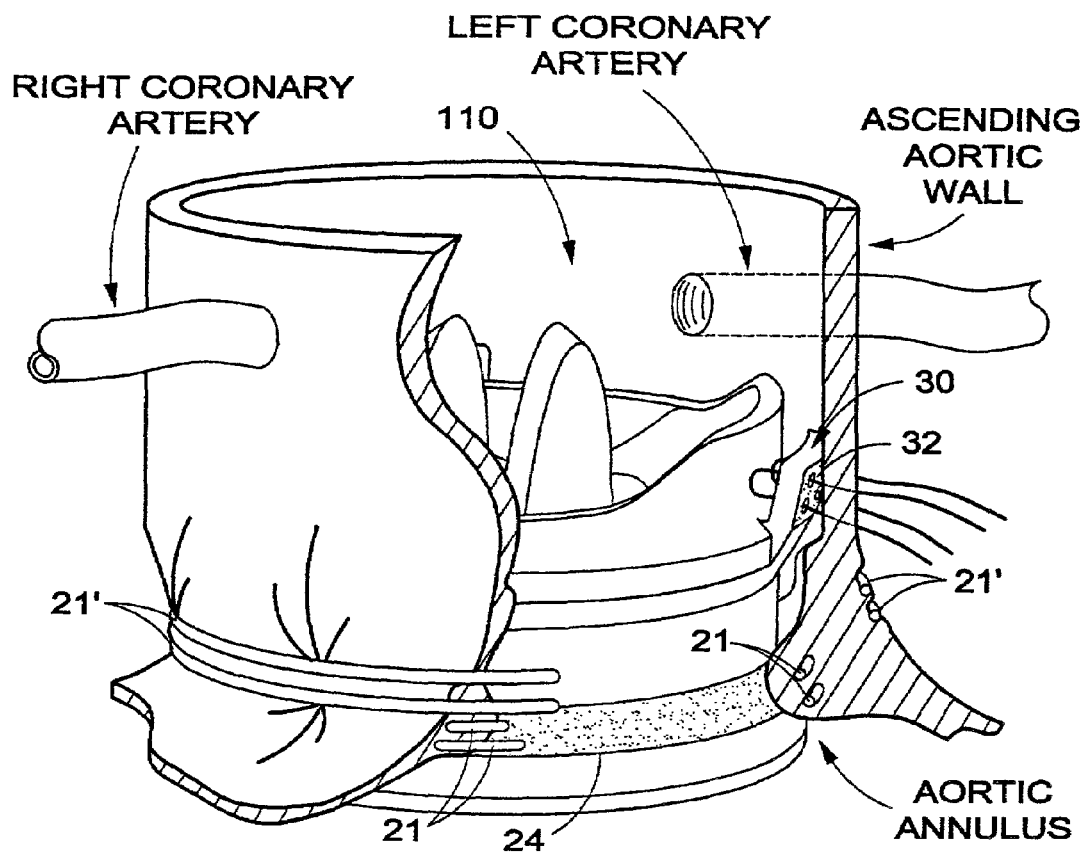
FIG. 2 schematically illustrates implantation of the valve of FIG. 1 relative to anatomic structures in a patient.

Growing tissue tends to adhere to each tissue adherence area 32, which comprises unpolished pyrolytic carbon in certain preferred embodiments of valve 110. On the other hand, growing tissue tends not to adhere to valve body 25, except for tissue adherence band 24, or to adhere relatively less strongly than to area 32. Valve body 25, except for tissue adherence band 24, comprises polished pyrolytic carbon in such preferred embodiments. Note that the edges of tissue adherence areas 32 are generally blocked from contact with a patient's blood stream after implantation by overlap of the patient's tissue, which is drawn into close contact with area 32 by sutures threaded through holes 33 and adjacent tissue as schematically illustrated in FIG. 2.

Similar blocking of blood stream contact with non-fibrous circumferential tissue adherence band 24 occurs after implantation in an analogous manner in preferred embodiments of valves of the present invention. For example, during implantation of valve 110, the patient's annular tissue is drawn into close contact with band 24 within groove 20 by tension in circumferential cords 21 and/or 21' (which are schematically illustrated in FIG. 2). Except for band 24, which in certain preferred embodiments comprises unpolished pyrolytic carbon, groove 20 preferably comprises polished pyrolytic carbon in these same embodiments. Thus, the polished portions of groove 20 that lie adjacent to band 24 on either side of the unpolished band effectively block band 24 from contact with a patient's blood stream after implantation. Where more complete blocking of blood stream contact with tissue adherence areas of a valve is desired, shield margins may be employed. Preferred locations for such use of shield margins include, but are not limited to, the tissue contact surfaces of posts and cleats. Such shield margins function as smooth sealing tissue interfaces that lessen the risk of thromboembolism and/or infection by preventing a patient's blood flow from contacting tissue adherence areas. Pyrolytic carbon, which is a material favored for preferred embodiments of valves of the present invention, can function both as a shield margin (when polished) and as a non-fibrous tissue adherence area (when unpolished). More generally, shielded inserts may comprise tissue adherence areas circumscribed or partially bordered by a shield margin wherein the tissue adherence areas may comprise any fibrous or non-fibrous biologically-compatible material that promotes tissue growth which adheres to the tissue adherence areas in preference to the shield margin.

Figure 1A:
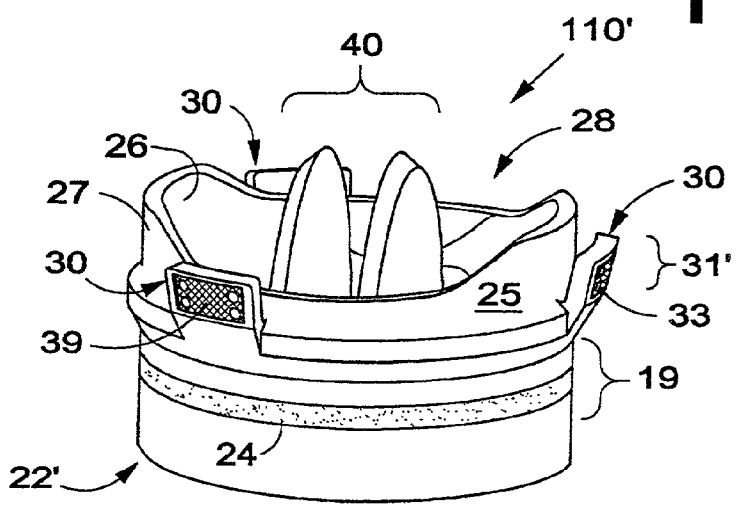
FIG. 1A schematically illustrates a valve similar to that shown in FIG. 1, but differing in having a non-flared inlet end and shielded fibrous inserts on tissue contact surfaces of the semirigid flange posts.
Figure 1B:
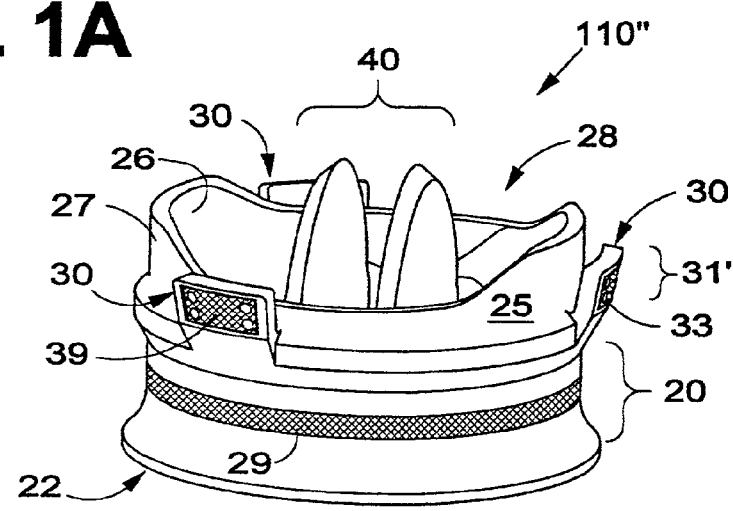
FIG. 1B schematically illustrates a valve similar to that shown in FIG. 1, but differing in having shielded fibrous inserts on tissue contact surfaces of the semirigid flange posts, as well as a fibrous tissue adherence band on the external circumferential valve body groove.

Examples of shielded fibrous inserts 39 are shown schematically on posts 31' in FIGS. 1A and 1B. Posts 31' on valves 110' and 110" are similar to posts 31 shown in FIG. 1 except that posts 31' comprise shielded fibrous inserts 39 instead of the non-fibrous tissue adherence areas 32. Note also that FIG. 1A schematically illustrates a valve 110' having a non-flared inlet end 22' (and therefore no groove 20 but a circumferential sealing ring 19 instead). FIG. 1B schematically illustrates a valve 110" similar to that shown in FIG. 1A, but having a flared inlet end 22, and also having a fibrous tissue adherence band 29 instead of a non-fibrous tissue adherence band 24.

Note that since the three discontinuous arcuate flange portions 30 in FIG. 1 form part of groove 20, the groove 20 itself is nonuniform in shape. Nevertheless, after implantation of the valve 110, shown schematically in FIG. 2, a patient's natural aortic annulus is held securely positioned in groove 20 by sutures placed through holes 33 and extending generally radially through the patient's aortic commissures and/or through the patient's ascending aortic wall lying between the commissures.

As also seen in FIG. 2, a patient's natural aortic annulus tissue is drawn into sealing contact with non-fibrous tissue adherence band 24 within groove 20 by tension in circumferential cords 21 and/or 21'. Circumferential cords 21 lie generally within the aortic annulus tissue (e.g., in the form of purse-string sutures), while circumferential cords 21' lie generally on the outer surface of the ascending aorta. When drawn into sealing contact with circumferential non-fibrous tissue adherence band 24 within groove 20, the aortic annulus tissue preferably slightly overlaps the edges of non-fibrous band 24 providing blocking against blood stream contact with band 24.

Figure 3:
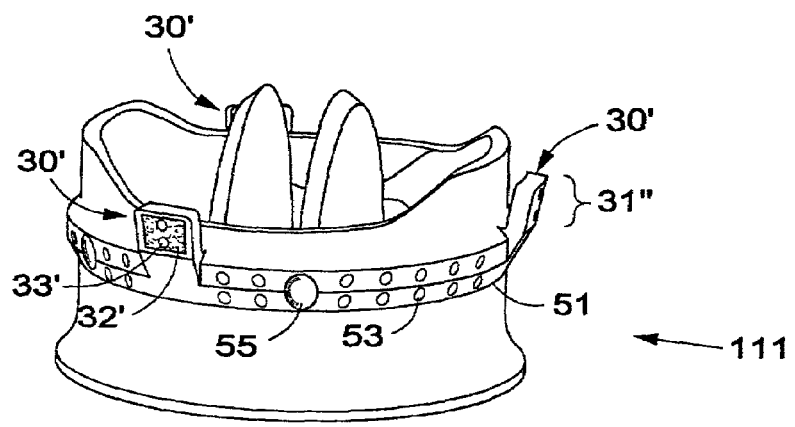
FIG. 3 schematically illustrates a valve similar to the valve of FIG. 1 but differing in having a discontinuous semirigid sewing flange having posts of alternative design in combination with a contiguous band semirigid sewing flange.
Figure 4:
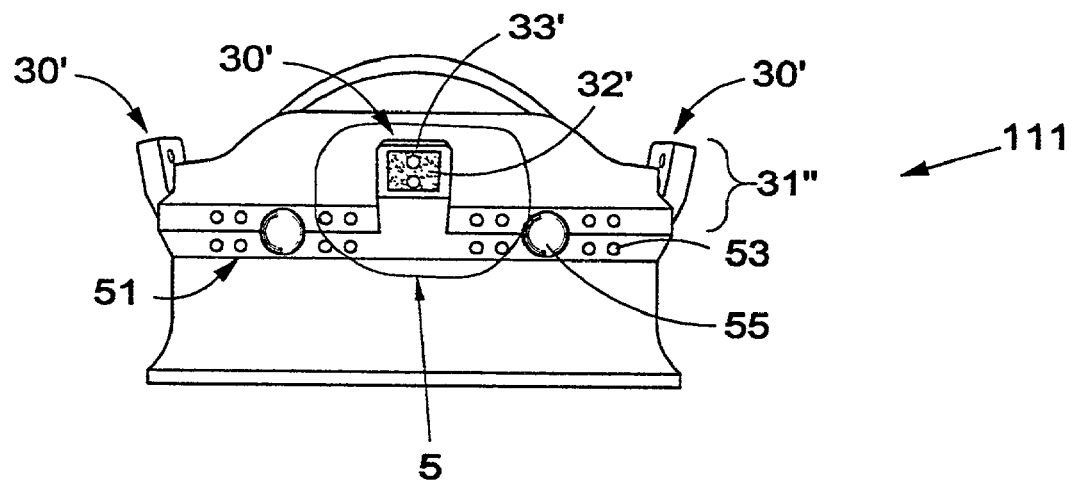
FIG. 4 schematically illustrates a side elevation of the valve of FIG. 3.
Figure 5:
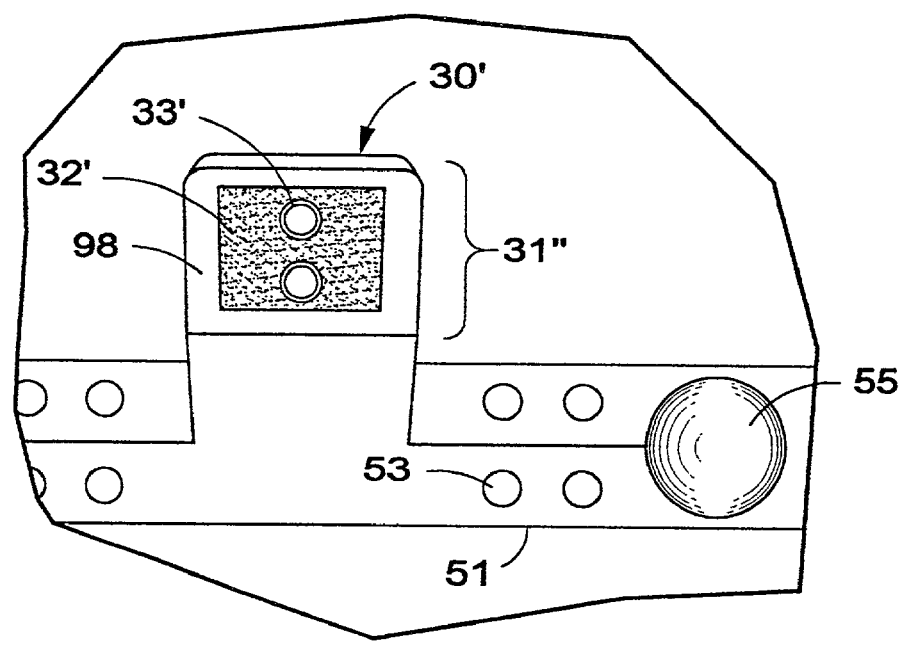
FIG. 5 schematically illustrates detail of the suture posts of the valves of FIGS. 3 and 4.

FIGS. 3 and 4 schematically illustrate different views of a valve 111 comprising a discontinuous semirigid sewing flange comprising the three arcuate portions 30', each portion 30' comprising a post 31" and each post 31" comprising two holes 33' and a shielded non-fibrous insert 32'. The three arcuate flange portions 30' are shown in combination with contiguous semirigid sewing flange ring 51. Flange ring 51 has a plurality of holes 53 and a plurality of thinned areas 55 to add flexibility to the ring. Flange ring 51 is included on valve 111 to provide flexibility for a surgeon to add sutures between holes 53 and the radially adjacent ascending aortic wall in a patient having diseased and/or anatomically anomalous commissures radially adjacent to the posts 31'. Note that the posts 31" with their holes 33' are non-coplanar with flange ring 51 with its holes 53. FIG. 5 schematically illustrates detail of flange ring 51, holes 53 and thinned areas 55, together with an arcuate portion 30' that includes post 31", holes 33', and non-fibrous tissue adherence area 32' circumscribed by shield margin 98 to form a shielded non-fibrous insert. Note, however, that valve 111 has no circumferential tissue adherence band.

Figure 6:
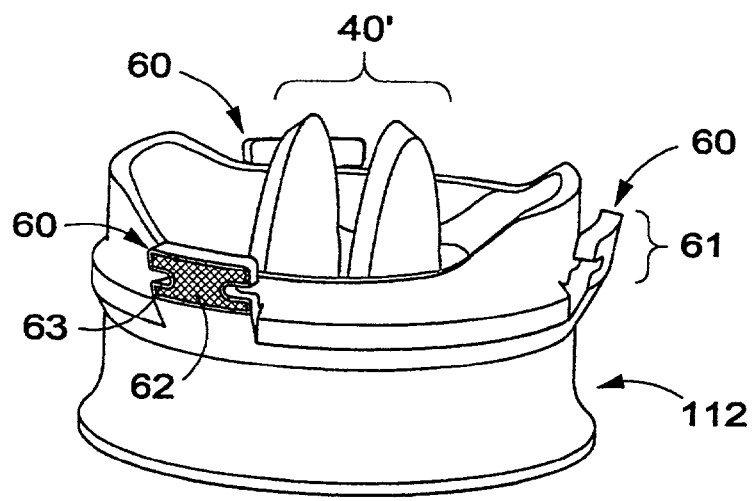
FIG. 6 schematically illustrates a prosthetic valve having suture cleats instead of suture posts.
Figure 7:
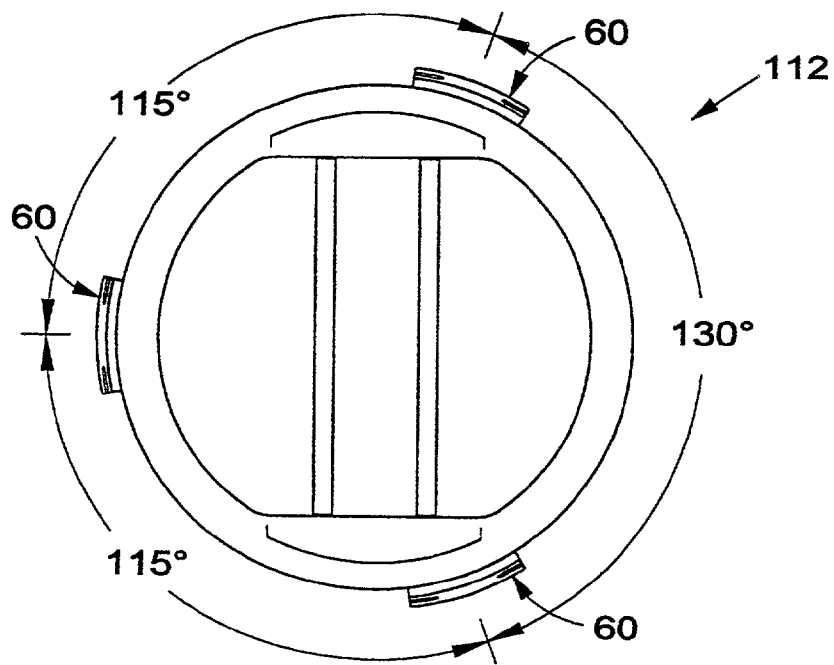
FIG. 7 schematically illustrates a typical example of the non-uniform spacing preferred between the suture cleats of the valve of FIG. 6, the cleat spacing approximating the spacing between a patient's corresponding commissures to which the cleats will be connected by interrupted sutures during implantation.
Figure 8:
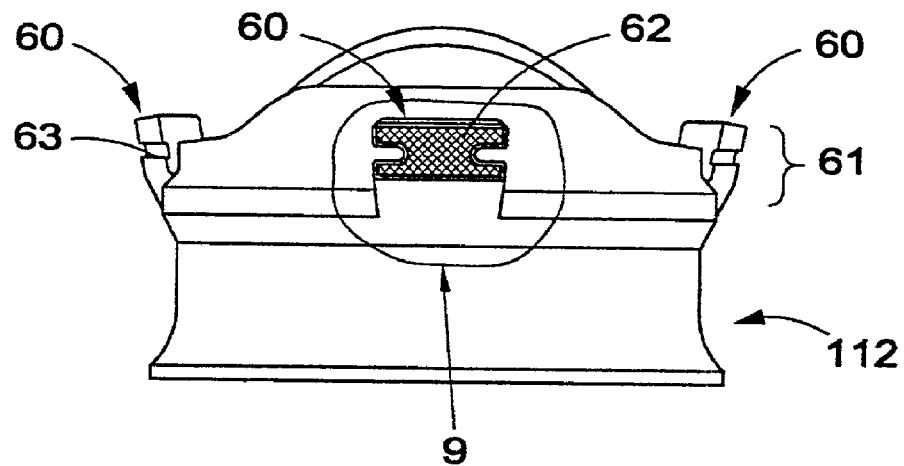
FIG. 8 schematically illustrates a side elevation of the valve of FIG. 6.
Figure 9:
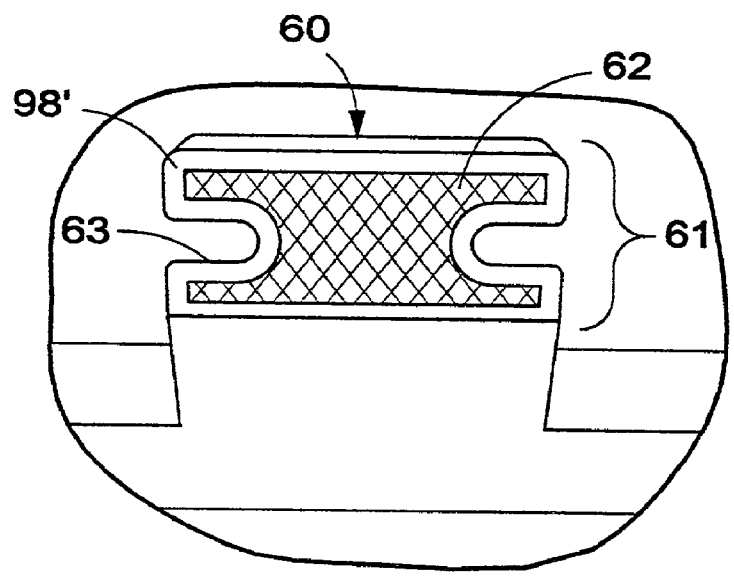
FIG. 9 schematically illustrates detail of the suture cleats of the valve of FIGS. 6, 7 and 8.
Figure 10:
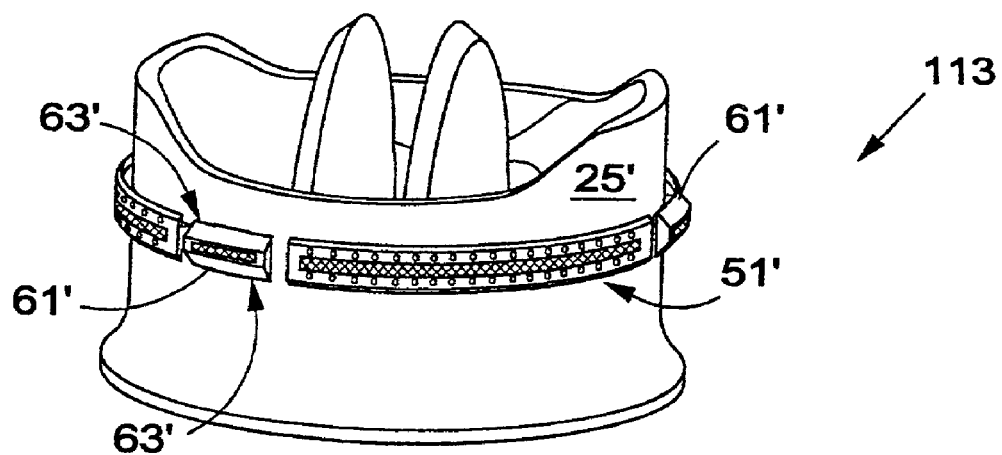
FIG. 10 schematically illustrates a prosthetic valve having a contiguous semirigid sewing flange in combination with suture cleats.
Figure 11:
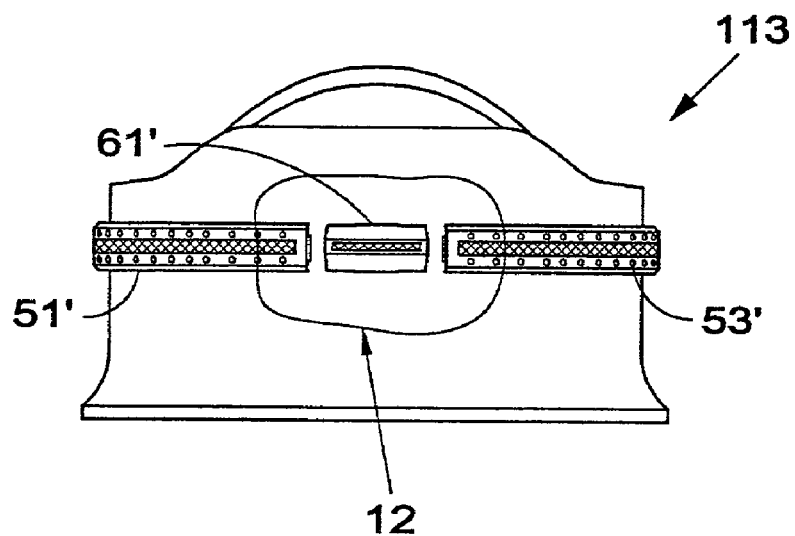
FIG. 11 schematically illustrates a side elevation of the valve of FIG. 10.
Figure 12:
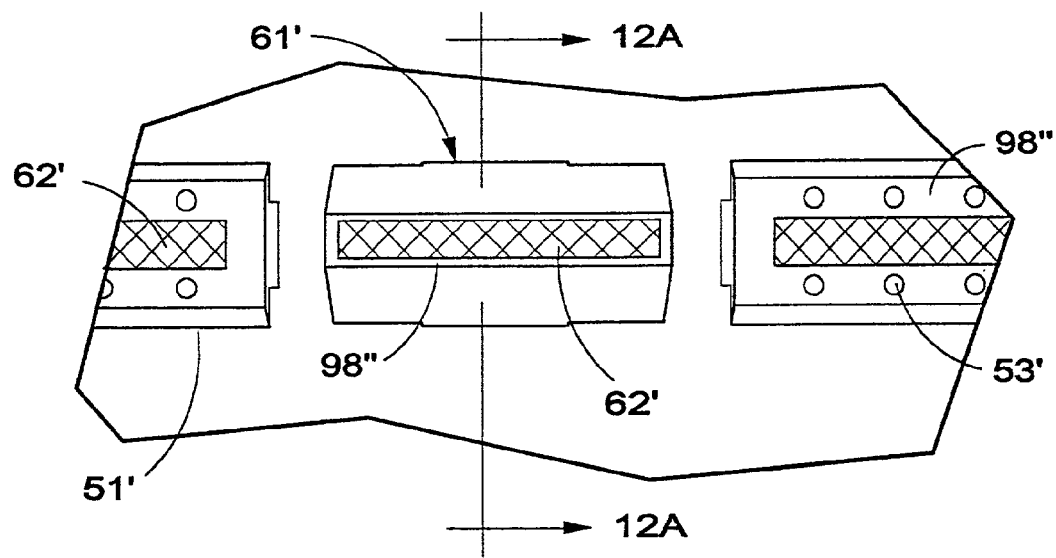
FIG. 12 schematically illustrates detail of the suture cleats of the valves of FIGS. 10 and 11.
Figure 12A:
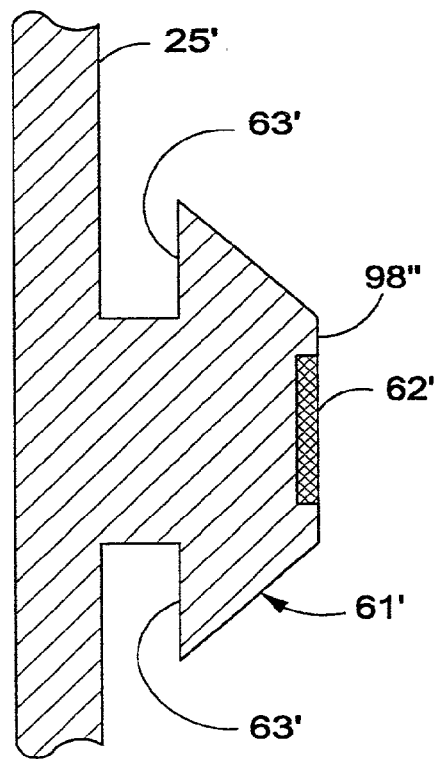
FIG. 12A schematically illustrates the indicated cross-section in FIG. 12.

FIGS. 6, 7, 8 and 9 schematically illustrate different views of a valve 112 comprising a discontinuous semirigid sewing flange comprising the three arcuate portions 60. Each arcuate portion 60 comprises a cleat 61 and each cleat 61 comprises two notches 63 and a fibrous tissue adherence area 62 circumscribed by shield margin 98' to form a shielded fibrous insert. FIG. 6 provides perspective and includes schematic representation of flow control means 40'. The plan view of FIG. 7 shows an example of the non-uniform spacing preferred between arcuate portions 60 to match the non-uniform spacing commonly found between commissures in patients needing prosthetic valve 112 implanted. FIG. 8 is a side elevation of valve 112 and FIG. 9 schematically illustrates detail of arcuate portions 60. Note that valve 112 has no circumferential tissue adherence band.

FIGS. 10, 11, 12 and 12A schematically illustrate different views of a valve 113 comprising a contiguous semirigid sewing flange 51' in combination with three cleats 61', each cleat 61' comprising two notches 63', a portion of fibrous tissue adherence area 62', and a portion of shield margin 98". Note that due to the relatively narrow tissue contact areas on cleats 61' and flange 51' in this valve embodiment, there is a need to maximize use of available areas on flange 51' and cleats 61' for tissue adherence and also to ensure strong tissue adherence in these areas. Thus, fibrous tissue adherence areas 62' with their shield margins 98" are themselves discontinuous, being found both on cleats 61' and sewing flange 51'. As seen in the cross-sectional view of FIG. 12A, fibrous tissue adherence area 62' comprises fibrous material that is itself adhered within a shallow depression formed in cleat 61'. Since they are not on a sealing ring, fibrous tissue adherence areas 62' do not constitute a circumferential tissue adherence band as in the present invention.

Also note that in this illustrated embodiment of a semirigid sewing flange, notches 63' are located in spaces between portions of each cleat 61' and the tubular valve body 25', rather than on the cleat edges as shown in FIGS. 6–9. The three cleats 61' are shown in combination with contiguous semirigid sewing flange ring 51', flange ring 51' having a plurality of holes 53'. But the three coplanar cleats 61' in this valve embodiment take the place of the plurality of thinned areas 55 shown in FIGS. 3, 4 and 5, functioning to provide needed flexibility in flange ring 51'. Analogous to the case of valve 111, flange ring 51' (with holes 53') is included on valve 113 to allow a surgeon to add sutures between holes 53' and the radially adjacent ascending aortic wall in a patient having diseased and/or anatomically anomalous commissures radially adjacent to the otherwise-preferred suture attachments on cleats 61'.

Figure 13:
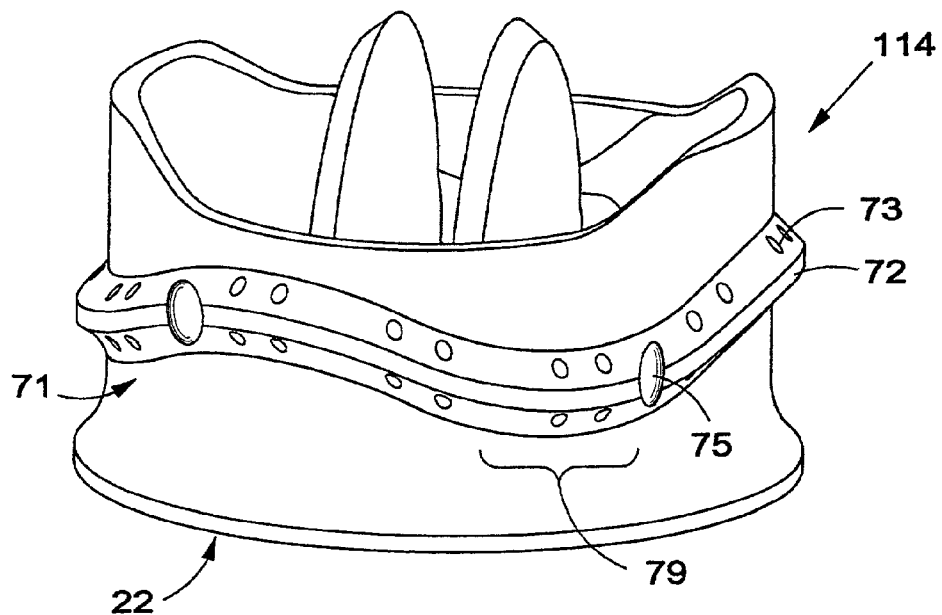
FIG. 13 schematically illustrates a prosthetic valve having a non-coplanar contiguous semirigid sewing flange.
Figure 14:
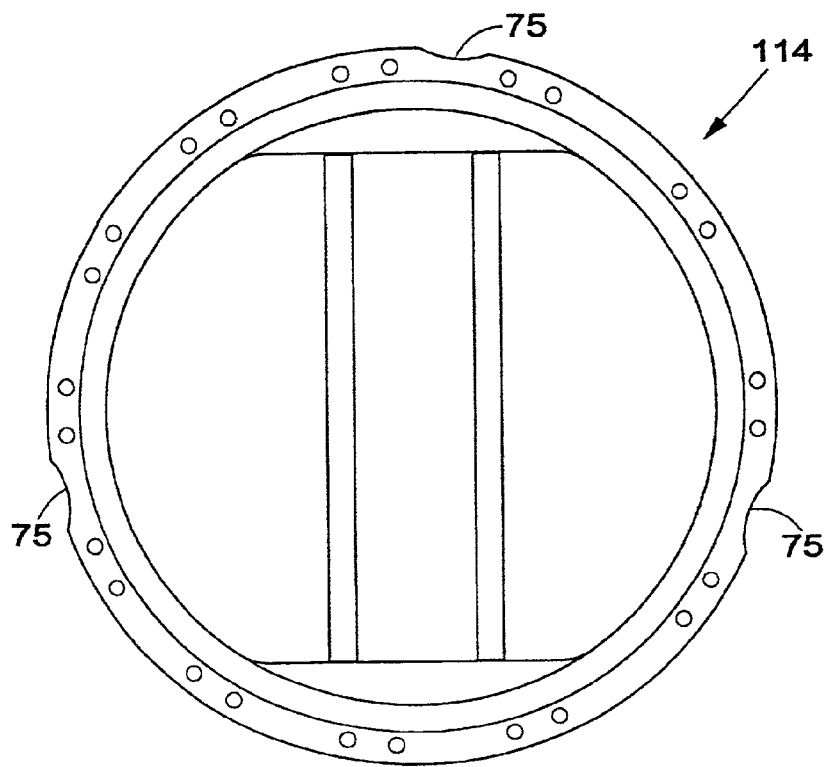
FIG. 14 schematically illustrates a plan view of the valve of FIG. 13.

FIGS. 13 and 14 schematically illustrate different views of a valve 114 comprising a non-coplanar contiguous semirigid sewing flange 71 comprising a non-coplanar circumferential tissue contact surface 72, a plurality of thinned areas 75 for added flexibility, and a plurality of holes 73. Note that there are no tissue adherence areas (either fibrous or non-fibrous) on either tissue contact surface 72 or between the flared inlet 22 and flange 71. The plan view of valve 114 shown in FIG. 14 schematically illustrates the thinned areas 75, while the view of FIG. 13 shows the non-coplanar embodiment of semirigid flange 71. The plurality of portions 79 of flange 71 (i.e., portions of flange 71 that are closest to flared inlet end 22 of valve 114) are preferably located so that two portions 79 will be proximal to and longitudinally aligned with the patient's respective (right and left) coronary artery ostia when the valve 114 is implanted. This provides additional flange clearance around the coronary arteries and reduces the likelihood that implantation of the valve will result in any compromise of coronary blood flow. Flange portions 79 and flared inlet end 22 are spaced sufficiently far from each other to accommodate a patient's aortic annulus between them.

Figure 15:
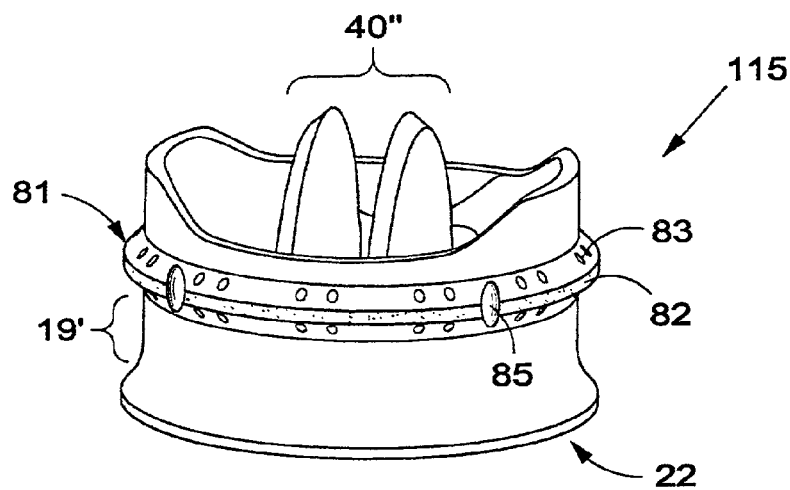
FIG. 15 schematically illustrates a prosthetic valve having a coplanar contiguous semirigid sewing flange.
Figure 16:
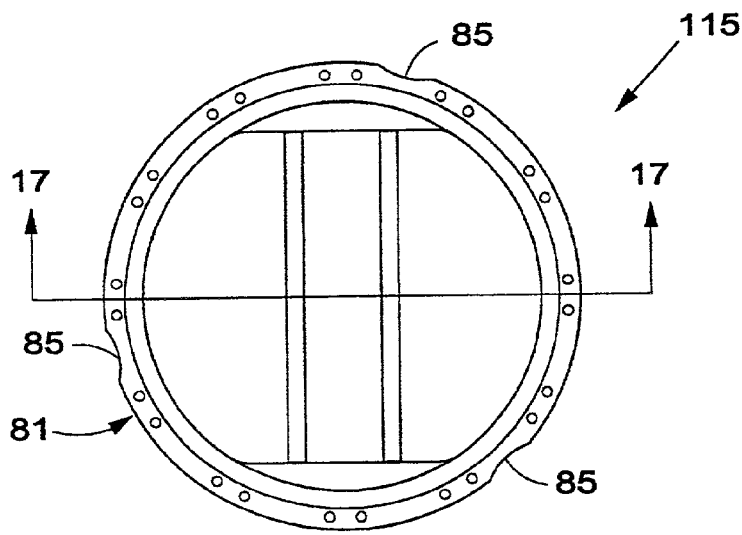
FIG. 16 schematically illustrates a plan view of the valve of FIG. 15.
Figure 17:
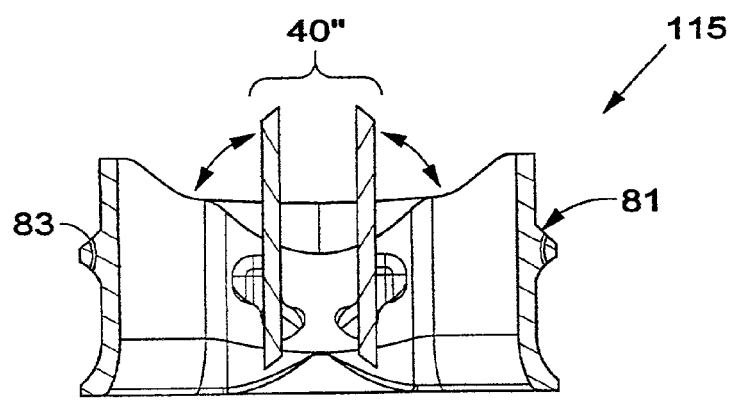
FIG. 17 schematically illustrates the indicated cross-sectional view of the valve of FIG. 16.

FIGS. 15, 16 and 17 schematically illustrate different views of a valve 115 comprising a coplanar contiguous semirigid sewing flange 81. Flange 81 comprises a coplanar circumferential non-fibrous tissue adherence band 82, a plurality of thinned areas 85 and a plurality of holes 83. Note, however, that there is no tissue adherence area in the sealing ring 19' between flange 81 and flared inlet 22. The plan view of valve 115 shown in FIG. 16 schematically illustrates the plurality of thinned areas 85, while the cross-sectional view of FIG. 17 shows the internal structure of a typical example embodiment of flow control means 40". The plurality of thinned areas 85 of flange 81 (i.e., portions of flange 81 least likely to interfere with coronary artery blood flow) are preferably located so that two thinned portions 85 will be proximal to the patient's coronary artery ostia when the valve 115 is implanted.

What is claimed is:

1. A prosthetic aortic mechanical valve, comprising
a substantially round tubular valve body, which body has a longitudinal axis, an outlet end, a flared inlet end, an inner surface, and an outer surface, said outer surface comprising a semirigid sewing flange and a circumferential groove on said outer surface, said groove lying between and spacing apart said flared inlet end and said semirigid sewing flange; and
flow control means within said tubular valve body for intermittently and reversibly sealing across said valve body inner surface to allow substantially unidirectional flow through said tubular valve body from said inlet end to said outlet end;
wherein said semirigid sewing flange comprises at least first and second flange portions which are spaced circumferential apart from each other and longitudinally from said flared inlet end, a plurality of said flange portions comprising at least one post for securing sutures, which post is spaced radially from said outer surface to permit the passage of sutures therebetween.

2. The aortic valve of claim 1 wherein said at least first and second flange portions are spaced between about 4 millimeters and about 12 millimeters from said flared inlet end.

3. The aortic valve of claim 1 wherein each post for securing sutures comprises a non-fibrous tissue adherence area.

4. The aortic valve of claim 3 wherein said groove comprises a non-fibrous circumferential tissue adherence band.

5. The aortic valve of claim 1 comprising first, second and third flange portions.

6. The aortic valve of claim 5 wherein said first and second flange portions subtend an angle at said valve body longitudinal axis of about 130 degrees.

7. The aortic valve of claim 6 wherein said second and third flange portions subtend an angle at said valve body longitudinal axis of about 115 degrees.

8. A prosthetic aortic mechanical valve, comprising
a substantially round tubular valve body, which body has a longitudinal axis, an outlet end, a flared inlet end, an inner surface, and an outer surface, said outer surface comprising a semirigid sewing flange and a circumferential groove on said outer surface, said groove lying between and spacing apart said flared inlet end and said semirigid sewing flange; and
flow control means within said tubular valve body, said flow control means for intermittently and reversibly sealing across said valve body inner surface to allow substantially unidirectional flow through said tubular valve body from said inlet end to said outlet end;
wherein said semirigid sewing flange comprises at least first and second flange portions which are spaced circumferentially apart from each other and longitudinally from said flared inlet end, a plurality of said flange portions comprising at least one cleat for securing sutures, which cleat is spaced radially from said outer surface to permit the passage of sutures therebetween.

9. The aortic valve of claim 8 wherein said at least first and second flange portions are spaced between about 4 millimeters and about 12 millimeters from said flared inlet end.

10. The aortic valve of claim 8 wherein each cleat for securing sutures comprises a non-fibrous tissue adherence area.

11. The aortic valve of claim 10 wherein said groove comprises a non-fibrous circumferential tissue adherence band.

12. The aortic valve of claim 8 comprising first, second and third flange portions.

13. The aortic valve of claim 12 wherein said first and second flange portions subtend an angle at said valve body longitudinal axis of about 130 degrees.

14. The aortic valve of claim 13 wherein said second and third flange portions subtend an angle at said valve body longitudinal axis of about 115 degrees.

15. The aortic valve of claim 8 wherein said tubular valve body comprises pyrolytic carbon, wherein each cleat for securing sutures comprises a non-fibrous tissue adherence area comprising unpolished pyrolytic carbon, and wherein said circumferential groove on said valve body comprises a non-fibrous tissue adherence band, said band comprising unpolished pyrolytic carbon.

16. A prosthetic aortic mechanical valve, comprising
a substantially rigid tubular valve body having an inlet and an outlet and inner and outer surfaces;
internal flow control means in contact with said inner surface which establishes unidirectional blood flow through said valve body;
an external discontinuous semirigid sewing flange disposed circumferencially about said outer surface and having portions spaced radially from said surface for securing said valve body in a patient; and
a sealing ring comprising an external continuous circumferential non-fibrous tissue adherence band on said outer surface of said valve body at a location between said inlet and said sewing flange and spaced longitudinally from both said inlet and said sewing flange.

17. The prosthetic valve of claim 16 wherein said se rigid sewing flange portions comprise a plurality of non-fibrous tissue adherence areas on tissue contact surfaces on said radially spaced portions.

18. A prosthetic aortic mechanical valve comprising
a tubular valve body made of pyrolytic carbon having a longitudinal axis, an outlet end, a flared inlet end, an inner surface, and an outer surface, said outer surface comprising a semirigid sewing flange and being formed with a circumferential groove, said groove lying between and spacing apart said flared inlet end and said semirigid sewing flange and including a tissue adherence band of unpolished pyrolitic carbon; and
flow control means within said tubular valve body for intermittently and reversibly sealing across said valve body inner surface to allow substantially unidirectional flow through said tubular valve body from said inlet end to said outlet end;
wherein said semirigid sewing flange comprises at least first and second portions which are spaced circumferentially apart from each other and spaced longitudinally from said flared inlet end, a plurality of said flange portions each comprising at least one post for securing sutures, each said post comprising a non-fibrous tissue adherence area comprising unpolished pyrolytic carbon.

19. The aortic valve of claim 18 wherein said at least first and second flange portions are longitudinally spaced between about 4 millimeters and about 12 millimeters from said flared inlet end.

20. The aortic valve of claim 18 wherein each said post for securing sutures comprises a non-fibrous tissue adherence area.

21. The aortic valve of claim 18 comprising first, second and third flange portions.

22. The aortic valve of claim 21 wherein said first and second flange portions subtend an angle at said valve body longitudinal axis of about 130 degrees.

23. The aortic valve of claim 22 wherein said second and third flange portions subtend an angle at said valve body longitudinal axis of about 115 degrees.

24. A prosthetic aortic mechanical valve, which valve comprises
a substantially rigid tubular valve body of substantially circular cross section, which body has a longitudinal axis, an outlet end, a flared inlet end, an inner surface and an outer surface, said valve body comprising a flange extending radially outward from the outer surface for attachment of said valve body in the aorta of a patient by sutures extending through the patient's tissue,
flow control means within said tubular valve body for intermittently and reversibly sealing across said valve body inner surface to establish substantially unidirectional flow through said tubular valve body from said inlet end to said outlet end; and
a circumferential continuous non-fibrous tissue adherence band circumscribing said outer surface of said valve body at a location between and spaced apart from said inlet end and said attachment flange.

25. The aortic valve of claim 24 wherein said attachment flange comprises at least first and second flange portions which are spaced circumferentially apart from each other and are formed with openings or notches for securing sutures, said flange portions extending obliquely from said outer valve body surface and in a downstream direction.

26. The aortic valve of claim 25 wherein said at least first and second flange portions are spaced at least about 4 millimeters from said inlet end, and
each of said flange portions comprises a non-fibrous tissue adherence area adjacent said openings or notches for securing sutures.

27. The aortic valve of claim 24 comprising first, second and third flange portions.

28. The aortic valve of claim 27 wherein said first and second flange portions subtend an angle of about 130 degrees at said valve body longitudinal axis.

29. The aortic valve of claim 28 wherein said second and third flange portions subtend an angle of about 115 degrees at said valve body longitudinal axis.

30. The aortic valve of claim 24 wherein said flange portions are formed integral with valve body and so as to be semirigid.

31. The aortic valve of claim 24 wherein said tissue adherence band is located generally centrally within a groove that extends to said inlet end which is flared outward.

* * * * *